(12) United States Patent
Guerer et al.

(10) Patent No.: US 9,618,471 B2
(45) Date of Patent: Apr. 11, 2017

(54) CIRCUIT SYSTEM FOR MEASURING A SENSOR ELEMENT CAPACITANCE

(71) Applicant: Robert Bosch GmbH, Stuttgart (DE)

(72) Inventors: Metin Guerer, Ludwigsburg (DE);
Norbert Schneider, Tiefenbronn (DE);
Karl Wenzel, Stuttgart (DE);
Axel-Werner Haag, Stuttgart (DE);
Rolf Reischl, Stuttgart (DE)

(73) Assignee: ROBERT BOSCH GMBH, Stuttgart (DE)

( * ) Notice: Subject to any disclaimer, the term of this patent is extended or adjusted under 35 U.S.C. 154(b) by 253 days.

(21) Appl. No.: 14/398,091

(22) PCT Filed: Apr. 4, 2013

(86) PCT No.: PCT/EP2013/057091
§ 371 (c)(1),
(2) Date: Oct. 30, 2014

(87) PCT Pub. No.: WO2013/164152
PCT Pub. Date: Nov. 7, 2013

(65) Prior Publication Data
US 2015/0107337 A1    Apr. 23, 2015

(30) Foreign Application Priority Data

May 4, 2012   (DE) .................. 10 2012 207 430

(51) Int. Cl.
*G01N 5/02*     (2006.01)
*G01N 7/00*     (2006.01)
(Continued)

(52) U.S. Cl.
CPC .................. *G01N 27/223* (2013.01)

(58) Field of Classification Search
USPC ............. 73/65.05, 29.05; 324/676, 678
See application file for complete search history.

(56) References Cited

U.S. PATENT DOCUMENTS 4,398,091 A * 8/1983 Passaro ............ G01N 21/3504
250/343
5,343,157 A * 8/1994 Deschamps ........ G01R 27/2605
324/678

(Continued)

FOREIGN PATENT DOCUMENTS

CN    1576861 A    2/2005
CN    201382977 Y    1/2010
(Continued)

*Primary Examiner* — Clayton E Laballe
*Assistant Examiner* — Warren K Fenwick
(74) *Attorney, Agent, or Firm* — Gerard Messina

(57) ABSTRACT

A circuit system for measuring a sensor element capacitance of a sensor element, in particular of a capacitive humidity sensor, including: the sensor element, which has the sensor element capacitance; a charge storage element, which is connected directly, or only via a resistor element, in series to the sensor element; and a control unit, which is configured to charge the charge storage element to a reference voltage and to successively transfer the charge via the sensor element capacitance until the charge storage element has reached a particular comparison voltage, the sensor element number of transfer processes thus ascertained representing information about the sensor element capacitance of the sensor element.

8 Claims, 3 Drawing Sheets

(51) Int. Cl.
*G01N 9/36* (2006.01)
*G01N 19/10* (2006.01)
*G01N 27/22* (2006.01)

(56) References Cited

U.S. PATENT DOCUMENTS

| | | | | |
|---|---|---|---|---|
| 7,084,644 B2 * | 8/2006 | Haider | ............... | G01R 27/2605 |
| | | | | 324/664 |
| 2011/0279131 A1 * | 11/2011 | Kim | ............... | G06F 3/044 |
| | | | | 324/679 |
| 2015/0084918 A1 * | 3/2015 | Ogirko | ............... | G06F 3/044 |
| | | | | 345/174 |

FOREIGN PATENT DOCUMENTS

| | | |
|---|---|---|
| CN | 201654137 U | 11/2010 |
| CN | 101943716 A | 1/2011 |
| DE | 102 04 572 | 7/2003 |
| DE | 10 2010 001377 | 8/2011 |
| EP | 1 341 306 | 9/2003 |

* cited by examiner

CIRCUIT SYSTEM FOR MEASURING A SENSOR ELEMENT CAPACITANCE

FIELD OF THE INVENTION

The present invention relates to circuit systems for measuring a sensor element capacitance, in particular to circuit systems which ascertain a capacitance with the aid of a microcontroller. The present invention further relates to circuit systems for capacitive humidity measurement.

BACKGROUND INFORMATION

Humidity measurements which indicate the humidity content of air are usually carried out with the aid of a capacitive humidity sensor. To determine the humidity in the air, the capacitance of the humidity sensor is ascertained at least relative to a reference capacitance and assigned to a humidity value.

A circuit system for measuring the humidity with the aid of a capacitive humidity sensor and with the aid of a microcontroller is discussed in U.S. Pat. No. 7,084,644 B2. To measure the humidity, the humidity sensor is repeatedly charged and discharged into a charge storage element and retrieved when the voltage across the charge storage element reaches or exceeds a threshold value. The number of discharging processes then represents a degree of the capacitance of the humidity sensor. To be able to carry out the discharging processes of the humidity sensor without discharging the charge storage element, a protective diode or a switch is provided, which disconnects the humidity sensor from the charge storage element at the point in time that the humidity sensor is charged.

SUMMARY OF THE INVENTION

According to the present invention, a circuit system for measuring a sensor element capacitance of a sensor element as described herein is provided.

Further advantageous embodiments of the present invention are specified in the further description herein.

According to one aspect, a circuit system for measuring a sensor element capacitance of a sensor element, in particular of a capacitive humidity sensor, is provided, including:
the sensor element, which has the sensor element capacitance;
a charge storage element, which is connected directly, or only via an ohmic resistor element, in series to the sensor element; and
a control unit, which is configured to charge the charge storage element to a reference voltage and to successively transfer the charge via the sensor element capacitance until the charge storage element has reached a particular comparison voltage, the sensor element number of transfer processes thus ascertained representing information about the sensor element capacitance of the sensor element.

One idea of the above-mentioned circuit system for measuring the capacitive sensor element is to be able to construct the circuit system using only passive components, such as capacitors and resistors, and a microcontroller, while a diode, or one or multiple switches for switching analog electrical variables, must be additionally provided outside the microcontroller in the circuit system according to the above-described related art.

By implementing the circuit system without the additional active components, on the one hand the complexity for manufacturing the circuit system may be reduced, and on the other hand the reliability of the same may also be increased.

This is essentially achieved by being able to disconnect the charge storage element from a shared reference potential in some switching states, whereby the evaluation is made possible without a switch or a switching diode.

Moreover, it may be provided that the control unit is discharged for transferring the sensor element capacitance and is subsequently connected in series to the charge storage element, so that the charge of the charge storage element is distributed to the charge storage element and the sensor element.

According to one specific embodiment, a reference element having a reference element capacitance may be provided. The control unit may moreover be configured to charge the charge storage element to a reference voltage and to successively transfer the charge via the reference element capacitance until the charge storage element has reached the particular comparison voltage, the reference element number of transfer processes with the aid of the reference element thus ascertained representing information about the reference element capacitance of the reference element, the sensor element capacitance being ascertainable from the value of the reference element capacitance, the reference element number and the sensor element number.

In particular, the control unit may be configured to carry out the charge transfer of the charge storage element with the aid of the sensor element capacitance and the charge transfer of the charge storage element with the aid of the sensor element capacitance in each case according to a first and a second predefined cycle time and, in order to ascertain the sensor element capacitance, to determine a reference element offset value by linear extrapolation of the reference element number of transfer processes with the aid of the reference element, as ascertained at the first and the second cycle time, to a cycle time of zero, and to determine a sensor element offset value by linear extrapolation of the sensor element number of transfer processes with the aid of the sensor element, as ascertained at the first and the second cycle time, to a cycle time of zero, and to apply the reference element offset value and the sensor element offset value to the reference element number and the sensor element number, prior to determining the sensor element capacitance.

Moreover, the control unit may correspond to a microcontroller, which includes terminals and a switch network, the switch network including, for each of the terminals, a first switch for connecting the terminal to a reference potential and a second switch for connecting the terminal to ground.

It may be provided that the sensor element and the charge storage element are connected in each case between two terminals of the control unit and are connected to a shared terminal.

Specific embodiments of the present invention are described in greater detail hereafter based on the accompanying drawings.

DETAILED DESCRIPTION

Figure 1:
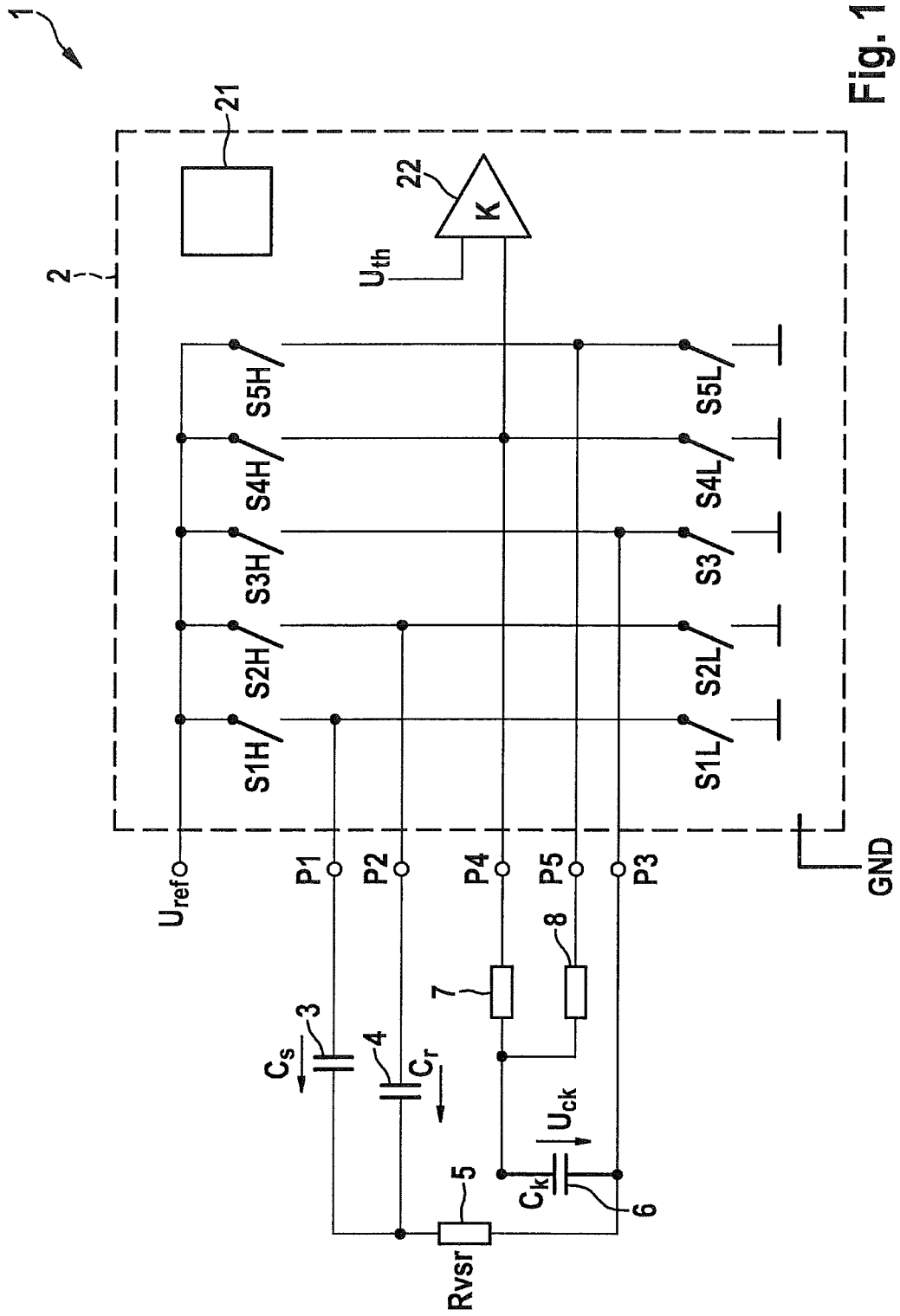
FIG. 1 shows a schematic illustration of a circuit system for measuring a sensor element capacitance.

FIG. 1 shows a circuit system 1 including a microcontroller 2, which has terminals P1 through P5. Microcontroller 2 includes a control unit 21 and first switch elements S1H through S5H to connect the appropriate terminal P1 through P5 to a reference voltage $U_{ref}$, or to disconnect them from the same, depending on the switching state. Reference voltage $U_{ref}$ may be generated internally in microcontroller 2 from a supply voltage or, as is shown in FIG. 1, may be supplied externally to microcontroller 2 via a separate reference voltage terminal. Second switch elements S1L through S5L are provided to connect the particular terminal P1 through P5 to ground GND, depending on the switching state. Control unit 21 is connected to control terminals of switch elements S1H through S5H, S1L through S5L in order to open and close the same.

Outside microcontroller 2, a first terminal of a capacitive sensor element 3, for example of a humidity sensor, having a sensor element capacitance $C_s$ is connected to first terminal P1. If sensor element 3 is a humidity sensor, the sensor element capacitance varies as a function of the relative humidity.

A first terminal of a capacitive reference element 4 having a reference element capacitance $C_r$ is connected to a second terminal P2 of microcontroller 2. The second terminals of sensor element 3 and of reference element 4 are interconnected and connected to a third terminal P3 of microcontroller 2 via a first resistor 5 (resistor element).

Moreover, a capacitive charge storage element 6 is provided, the first terminal of which is connected via a second resistor 7 to fourth terminal P4 of microcontroller 2. A second terminal of charge storage element 6 is connected to third terminal P3 of microcontroller 2.

The first terminal of charge storage element 6 is moreover connected to a thermal resistor element 8, the second terminal of which is connected to a fifth terminal P5 of microcontroller 2. Thermal resistor element 8 has a heat-dependent resistance value and may be situated on sensor element 3, so that a temperature equalization takes place between sensor element 3 and thermal resistor element 8.

Integrated into microcontroller 2, fourth terminal P4 is connected to a comparison element 22, which compares the voltage present at terminal P4 to a comparison voltage $U_{th}$, which is generated and provided internally in the microcontroller, and provides a corresponding comparison result signal E as the comparison result, depending on whether or not the voltage present at terminal P4 is greater than the comparison voltage $U_{th}$.

Figure 2:
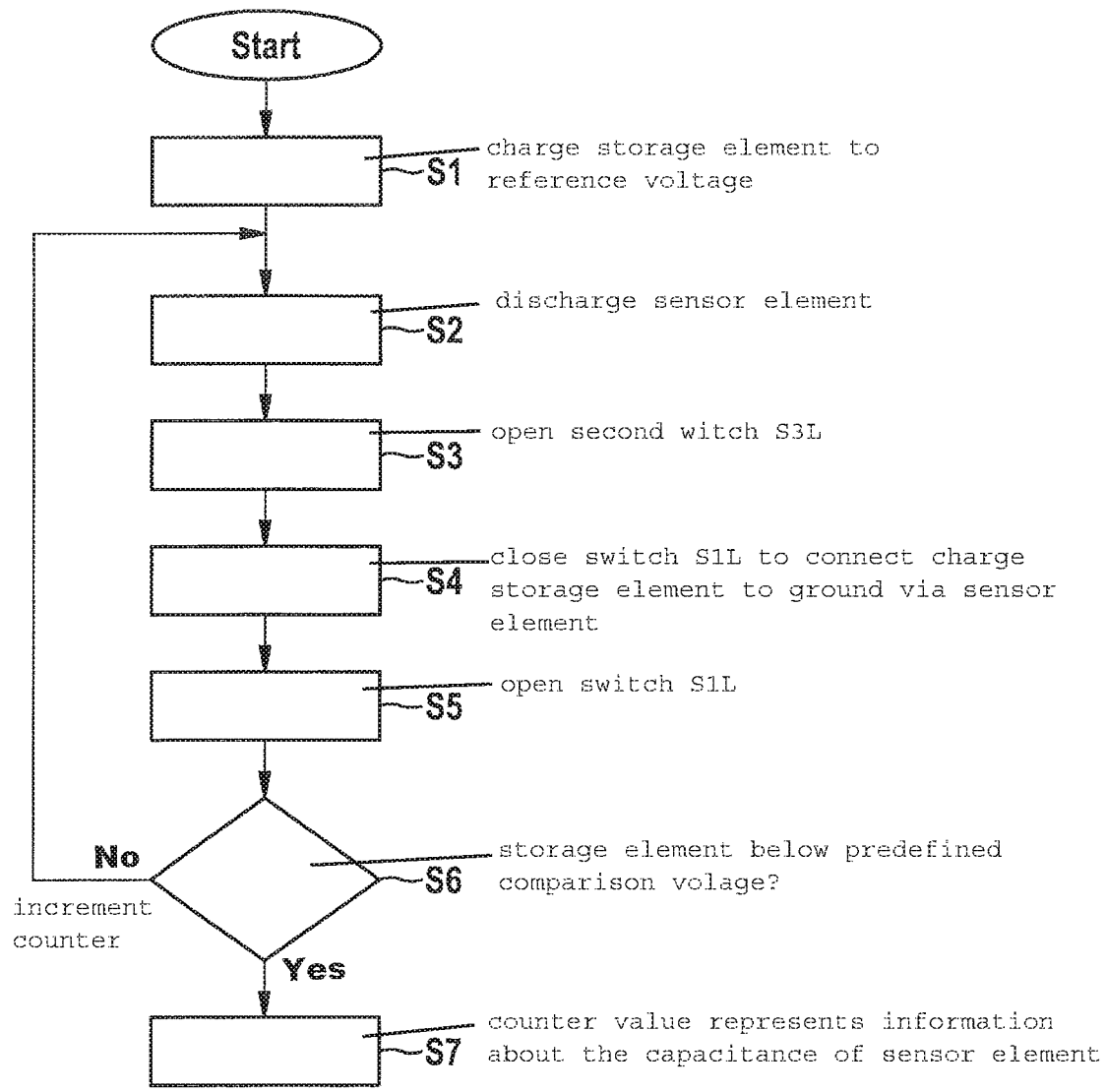
FIG. 2 shows a flow chart for illustrating the measuring method carried out by the microcontroller.

The method for measuring information about senor element capacitance $C_s$ is carried out by control unit 21 of microcontroller 2 and is described in greater detail in conjunction with the flow chart of FIG. 2.

In detail, the evaluation of sensor element 3 initially takes place in step S1 by charging charge storage element 6 to reference voltage $U_{ref}$ by closing at least first switches S4H, S5H connected to fourth and fifth terminals P4, P5 of microcontroller 2, and by connecting the second terminal of charge storage element 6, which is connected to third terminal P3 of microcontroller 2, to ground GND via closed second switch S3L. The switch positions are maintained at least until charge storage element 6 is fully charged to reference voltage $U_{ref}$. At the same time, a counter value of the counter situated in control unit 21 is reset to a fixed specified value, for example, to zero.

In a next step S2, second switch S1L connected to first terminal P1 of microcontroller 2 is closed, while second switch S3L assigned to third terminal P3 is or remains closed, in order to connect the two terminals of sensor element 3 to ground GND and thus discharge the sensor element. When step S2 is carried out for the first time for a measurement, it may also be carried out simultaneously with step S1.

In a next step S3, second switch S3L assigned to third terminal P3 is opened again and thereafter, in step S4, second switch S1L connected to first terminal P1 of microcontroller 2 is closed, in order to connect the second terminal of charge storage element 6 via sensor element 3 to ground GND.

The charge stored in charge storage element 6 is then distributed to sensor element 3 and charge storage element 6 in accordance with sensor element capacitance $C_s$ and the charge storage element capacitance, so that the charge stored in charge storage element 6 is incrementally reduced by a certain amount.

Thereafter, in step S5, second switches S1L are opened, and it is checked with the aid of comparison element 22 whether the voltage which is stored in charge storage element 6 drops below predefined comparison voltage $U_{th}$.

If it is established in step S6 that the voltage present at comparison element 22 has not dropped below comparison voltage $U_{th}$ (alternative: no), a counter value of the counter situated in control unit 21 is incremented, and above steps S2 through S5 are carried out repeatedly. If it is established in step S6 that the voltage present at comparison element 22 exceeds comparison voltage $U_{th}$ (alternative: yes), the counter value $n_{Cs}$ stored in the counter represents information about sensor element capacitance $C_s$ of sensor element 3.

The principle of measuring sensor element capacitance $C_s$ of sensor element 3 is that charge storage element capacitance $C_k$ of charge storage element 6 is charged to a constant voltage $U_{ref}$. Charge storage element capacitance $C_k$ of charge storage element 6 is then successively discharged with the aid of sensor element capacitance $C_s$ of sensor element 3 by consecutively withdrawing equal charge fractions, which result from the ratio of charge storage element capacitance $C_k$ of charge storage element 6 to sensor element capacitance $C_s$ of sensor element 3, from the capacitance of charge storage element 6 until voltage $U_{Ck}$ across charge storage element 6 has reached threshold voltage $U_{th}$. The number $n_{Cs}$ of switching cycles required for this discharge is counted by control unit 21 and is proportional to $1/C_s$ for a constant charge storage capacitance of charge storage element 6 and for a constant comparison voltage $U_{th}$.

Sensor element capacitance $C_s$ of sensor element 3 is dependent on the sensor temperature. For this reason, the temperature of sensor element 3 must also be detected for measuring the humidity, and must be considered in the calculation of the humidity.

The tolerances of charge storage element capacitance $C_k$ of charge storage element 6 may be equalized in a compensation process. Instead of using discharges by sensor element 3, for this purpose the above-described method is carried out using discharges of charge storage element 6 via reference element 4, which has a defined reference element capacitance $C_r$, and thus a number $n_{Cr}$ of reference cycles is ascertained, which are required to discharge charge storage element 6 to the comparison voltage. Sensor element capacitance $C_s$ of sensor element 3 is then derived from the ratio of the number $n_{Cs}$ of ascertained cycles for discharging charge storage element 6 with sensor element 3 to reference number $n_{Cr}$ of cycles for discharging charge storage element 6 with reference element 4, multiplied by reference element capacitance $C_r$ of reference element 4. In this way, the measurement is thus independent of charge storage element capacitance $C_k$ of charge storage element 6 and of applied reference voltage $U_{ref}$.

Consequently, for each measurement, the discharging of charge storage element 6 with the aid of sensor element 3 and the discharging of charge storage element 6 with the aid of reference element 4 are carried out consecutively to ascertain the particular cycle number $n_{Cs}$, $n_{Cr}$.

Residual currents which may occur in the circuitry may be ascertained and compensated for by using a calibration process with two different cycle times. The cycle time corresponds to the time duration during which the transfer process of step S4 is carried out. Cycle duration $t_{cyc}$ is to be constant for all transfer process of a measurement, both during the measurement of sensor element capacitance $C_s$ and for reference element capacitance $C_r$.

During the calibration process, the evaluation results are linearly extrapolated to a cycle time of 0 linear both during the above-mentioned sensor element capacitance measurement and during the reference element capacitance measurement with two different cycle times. In this way, the time-dependent influence of the residual currents on the counter results during counting of the discharge of charge storage element 6 with sensor element 3, or with reference element 4, may thus be ascertained, and the counter offset values may be ascertained by subtracting the through the linear extrapolation of the counter results at different cycle times to a cycle time of 0, the counter offset values being subtracted from counter values $n_{Cr}$, $n_{Cs}$ previously ascertained in the two measurements before they are divided to ascertain the sensor element capacitance.

A temperature evaluation may be carried out analogously to the procedure for ascertaining the sensor element capacitance of sensor element 3. However, charge storage element 6 is not discharged via sensor element 3, but via thermal resistor element 8, which has a positive temperature gradient (PTC). For this purpose, third terminal P3 of microcontroller 2 is connected via appropriate second switch S3L to ground GND, and fifth terminal P5 of microcontroller 2 is also connected to ground GND via appropriate second switch SSL, so that a discharge current flows across thermal resistor element 8, which continuously decreases voltage $U_{Ck}$ dropping across charge storage element 6. It is possible to measure the discharge time duration between the fully charged state of charge storage element capacitance $C_k$ and the discharge time duration until a point in time at which voltage $U_{Ck}$ reaches comparison voltage $U_{th}$. The discharge time duration may be counted and ascertained by a timer provided in microcontroller 2.

Figure 3:
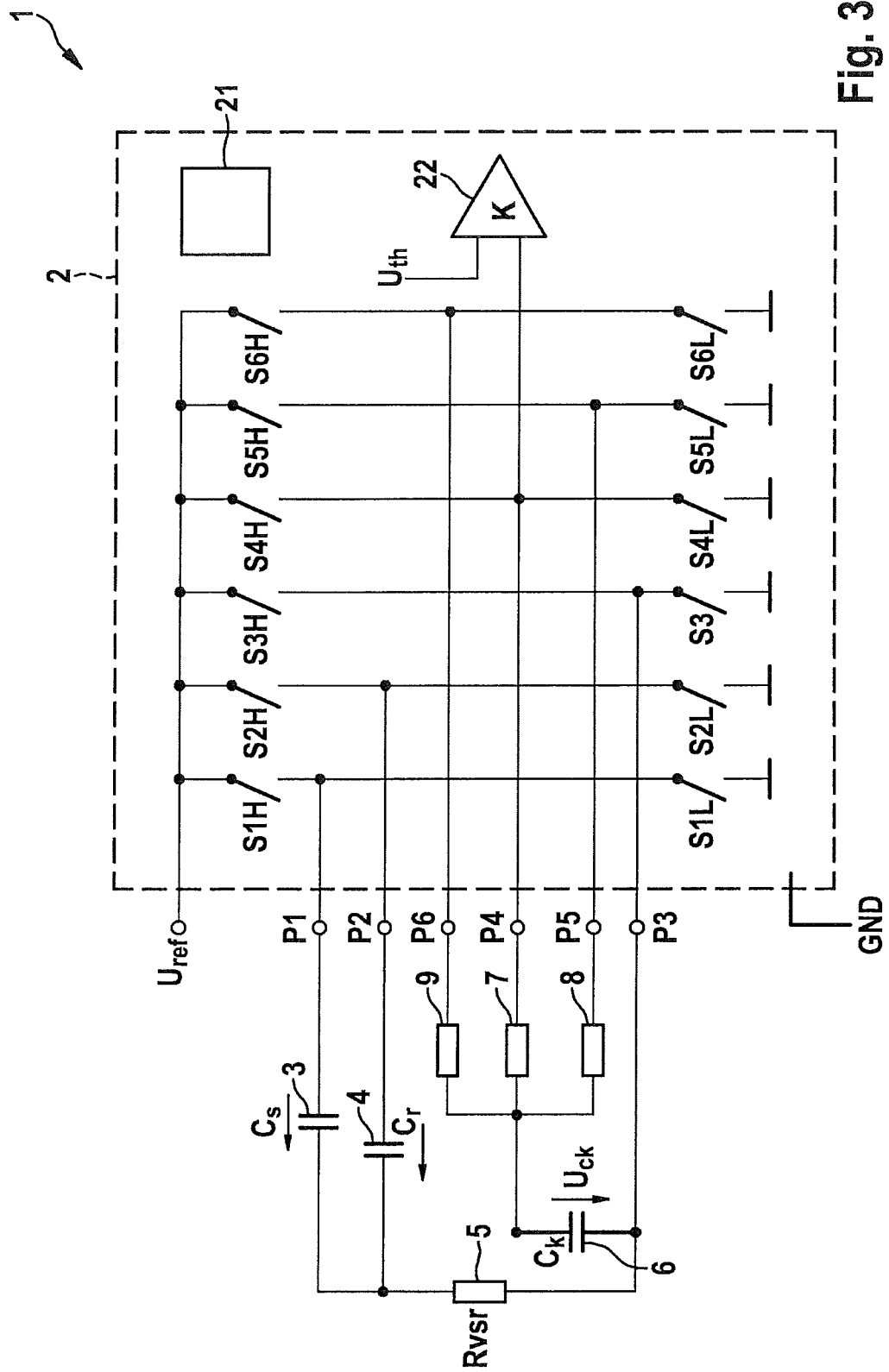
FIG. 3 shows a schematic illustration of a further circuit system for measuring a sensor element capacitance.

The tolerances of charge storage element capacitance $C_k$ of charge storage element 6 and reference voltage $U_{ref}$ are carried out in the compensation process with a reference resistance. In addition to the circuitry of the system shown in FIG. 1, for this purpose, as is shown in FIG. 3, a first terminal of reference resistor 9 is connected to the first terminal of charge storage element 6, the second terminal of the reference resistor being connected to a sixth terminal P6 of microcontroller 2. In the microcontroller, an appropriate first switch S6H for connecting to the supply potential and a second switch S6L for connecting to ground GND are provided for (assigned to) the sixth terminal. Second switch S6L assigned to sixth terminal P6 is closed for discharging charge storage element 6 via reference resistor 9, and time duration $t_r$ is determined until the voltage of charge storage element 6 drops below comparison voltage $U_{th}$. The time duration until charge storage element 6 is discharged via reference resistor 9 is also ascertainable by the internal timer. The exact resistance value of thermal resistor element 8 is ascertained from the ratio of the time durations thus measured, multiplied by the known resistance value of reference resistor 9.

Since the humidity-dependent parasitic capacitances of a printed circuit board which is used also influence the measurement when evaluating reference element 4, a humidity correction (cross-sensitivity correction) is required for this evaluation. For this purpose, different corrections are calculated as a function of a low-pass-filtered humidity signal, namely a humidity penetration time constant of the printed circuit board, for ascertaining the humidity content. The humidity sensitivity of the evaluation of reference element 4 affects the ascertainment of the humidity by sensor element 3 to a lesser degree, since the determination of sensor element capacitance $C_s$ of sensor element 3 is influenced by the same parasitic capacitances, and thus a large portion of the effect is automatically compensated for if the sensor element capacitance of sensor element 3 approximately corresponds to the reference element capacitance of reference element 4.

What is claimed is:

1. A circuit system for measuring a sensor element capacitance of a sensor, comprising:
    a capacitive sensor element having the sensor element capacitance;
    a charge storage element connected directly, or only via a resistor element, in series to the sensor element; and
    a control unit to charge the charge storage element to a reference voltage and to successively transfer the charge from the charge storage element via the sensor element until the charge storage element has reached a particular comparison voltage, the control unit configured to count the number of the successive transfers until the charge storage element has reached the particular comparison voltage, the number of successive transfers counted representing information about the sensor element capacitance of the sensor element.

2. The circuit system of claim 1, wherein, prior to the successive transfers, the sensor element is discharged and subsequently connected in series to the charge storage element, so that the charge of the charge storage element is distributed to the charge storage element and the sensor element during the transfers.

3. The circuit system of claim 1, wherein the sensor element is a capacitive humidity sensor.

4. A circuit system for measuring a sensor element capacitance of a sensor, comprising:
    a sensor element having the sensor element capacitance;
    a charge storage element connected directly, or only via a resistor element, in series to the sensor element;
    a control unit to charge the charge storage element to a reference voltage and to successively transfer the charge via the sensor element capacitance until the charge storage element has reached a particular comparison voltage, the sensor element number of transfer processes thus ascertained representing information about the sensor element capacitance of the sensor element; and
    a reference element having a reference element capacitance;
    wherein the control unit is configured to charge the charge storage element to a reference voltage and to successively transfer the charge via the reference element capacitance until the charge storage element reaches the particular comparison voltage, wherein the reference element number of transfer processes are ascertained with the reference element representing information about the reference element capacitance of the reference element, and wherein the sensor element capacitance is ascertainable from the value of the reference element capacitance, the reference element number and the sensor element number.

5. The circuit system of claim 4, wherein the control unit is configured to carry out the transfer of the charge storage element with the sensor element capacitance and the transfer of the charge storage element with the sensor element capacitance in each case according to a first and a second predefined cycle time and, to ascertain the sensor element capacitance, to determine a reference element offset value by linear extrapolation of the reference element number of transfer processes with the reference element, as ascertained at the first and the second cycle time, to a cycle time of zero, and to determine a sensor element offset value by linear extrapolation of the sensor element number of transfer processes with the sensor element, as ascertained at the first and the second cycle time, to a cycle time of zero, and to apply the reference element offset value and the sensor element offset value to the reference element number and the sensor element number, prior to determining the sensor element capacitance.

6. A circuit system for measuring a sensor element capacitance of a sensor, comprising:
 a sensor element having the sensor element capacitance;
 a charge storage element connected directly, or only via a resistor element, in series to the sensor element; and
 a control unit to charge the charge storage element to a reference voltage and to successively transfer the charge via the sensor element capacitance until the charge storage element has reached a particular comparison voltage, the sensor element number of transfer processes thus ascertained representing information about the sensor element capacitance of the sensor element;
 wherein the control unit is included in a microcontroller having terminals and a switch network, the switch network for each of the terminals including a first switch for connecting the terminal to a first potential, and a second switch for connecting the terminal to a second potential.

7. The circuit system of claim 6, wherein the sensor element and the charge storage element are connected in each case between two terminals of the control unit and are connected to a shared terminal.

8. A circuit system for measuring a sensor element capacitance of a sensor, comprising:
 a sensor element having the sensor element capacitance;
 a charge storage element connected directly, or only via a resistor element, in series to the sensor element; and
 a control unit to charge the charge storage element to a reference voltage and to successively transfer the charge via the sensor element capacitance until the charge storage element has reached a particular comparison voltage, the sensor element number of transfer processes thus ascertained representing information about the sensor element capacitance of the sensor element;
 wherein the control unit is included in a microcontroller having terminals and a switch network, the switch network for each of the terminals including a first switch for connecting the terminal to a first potential, which is a reference voltage, and a second switch for connecting the terminal to a second potential.

* * * * *